| United States Patent [19] | [11] 3,991,176 |
|---|---|
| Rubino | [45] Nov. 9, 1976 |

[54] ALUMINUM-ZIRCONIUM ANTI-PERSPIRANT SYSTEMS WITH HYDROXY CARBOXYLIC COMPOUNDS

[75] Inventor: Andrew M. Rubino, New Providence, N.J.

[73] Assignee: Armour Pharmaceutical Company, Phoenix, Ariz.

[22] Filed: Jan. 16, 1974

[21] Appl. No.: 433,931

Related U.S. Application Data

[63] Continuation-in-part of Ser. No. 418,712, Nov. 23, 1973.

[52] U.S. Cl. .............................. 424/47; 260/448 C; 260/448 R; 424/66, 67, 68
[51] Int. Cl.$^2$ ...................... A61K 7/00; A61K 9/00
[58] Field of Search ........................... 424/68, 47, 424/448 C, 66, 67, 448; 260/448 C, 448 R, 429.3, 429.9

[56] References Cited
UNITED STATES PATENTS

| | | | |
|---|---|---|---|
| 3,553,316 | 1/1971 | Rubino | 424/66 X |
| 3,712,948 | 1/1973 | Halpern et al. | 424/68 |
| 3,734,940 | 5/1973 | Rubino | 424/68 |

*Primary Examiner*—Helen M. S. Sneed
*Attorney, Agent, or Firm*—Frank T. Barber; William W. Schwarze

[57] ABSTRACT

Anti-perspirant complexes are provided which comprise a combination of a basic aluminum compound, a zirconium compound and a hydroxy carboxylic compound which may be a non-toxic salt of a hydroxy carboxylic acid, a non-toxic salt of an aluminum chelate of a hydroxy carboxylic acid, a codried mixture of aluminum hydroxide with a non-toxic salt of an aluminum chelate of a hydroxy carboxylic acid, or mixtures thereof. The various components are present in the complex in amounts such that the Al/Zr mol ratio is about 10:1 to 1:10 and the pH of an aqueous solution containing 5 to 15 weight percent of the complex (based on the oxides of aluminum and zirconium) is at least about 3. The complexes may be used in conventional anti-perspirant forms, including aqueous solutions, aerosol sprays (including powder-in-oil aerosol sprays), as well as creams, lotions and cream sticks.

16 Claims, No Drawings

ALUMINUM-ZIRCONIUM ANTI-PERSPIRANT SYSTEMS WITH HYDROXY CARBOXYLIC COMPOUNDS

CROSS-REFERENCE TO RELATED APPLICATIONS

This application is a continuation-in-part of my copending application Ser. No. 418,712, filed Nov. 23, 1973, entitled "Aluminum Zirconium Antiperspirant Systems with Salts of Amino Acids".

BACKGROUND OF THE INVENTION

The present invention relates to aluminum-zirconium anti-perspirant systems with hydroxy carboxylic compounds. More particularly, the invention is directed to water soluble complexes of zirconium which have a sufficiently high pH to be acceptable in anti-perspirant formulations for application to the human axilla.

It has been known in the art for some time that zirconium salts provide exceptionally effective anti-perspirant properties. Such zirconium compounds have included particularly the acidic zirconium salts, such as zirconium oxy chloride or zirconyl chloride, zirconium hydroxy chloride, and other halide and sulfate substitutes of the salts. However, the zirconium salts are extremely acidic and irritating to the skin. For example, a solution of zirconyl chloride which is effective as an anti-perspirant has a pH of only about 0.8 and a solution of zirconyl hydroxy chloride which is effective as an anti-perspirant has a pH of only about 1.2. As a result, it is necessary to buffer these solutions up to a pH which is suitable for application to the human skin, i.e., up to at least about 3 to 5.

A number of prior attempts have been made in the art to buffer solutions of zirconium salts or to form zirconium complexes which take advantage of the effectiveness of zirconium compounds. One early attempt included the development of sodium zirconium lactate for use in cologne-stick type formulations. This lactate complex salt was sufficiently alkaline (pH 8.5), but was ineffective as an anti-perspirant, and was repeatedly implicated in the generation of "zirconium granulomas" in some users.

Other attempts to make use of the acidic zirconium salts involved the buffering of solutions of these salts with urea (see U.S. Pat. No. 2,814,584 to Daley) or water soluble amino acids (see U.S. Pat. Nos. 2,814,585 to Daley and 2,854,382 to Grad) or aluminum hydroxy halides (see U.S. Pat. No. 2,906,668 to Beekman).

More recently, various derivatives have been formed incorporating zirconium compounds, including the amine-amide derivatives of U.S. Pat. No. 3,407,254 to Siegal et al., and the polyhydroxy derivatives of U.S. Pat. No. 3,405,153 to Jones and Rubino.

While the above attempts have succeeded in varying degrees in alleviating the acidic characteristics of zirconium salts, an entirely satisfactory zirconium anti-perspirant composition has not been previously found. Thus, it is desired to find a zirconium anti-perspirant composition which effectively makes use of the exceptional anti-perspirant properties of the zirconium, while at the same time offsetting the acidity and other disadvantages of zirconium salts.

SUMMARY OF THE INVENTION

According to the present invention, it has been found that effective anti-perspirant compositions may be achieved by forming a water soluble complex which comprises a combination of a basic aluminum compound, a zirconium compound selected from zirconium oxy salts, zirconium hydroxy salts and mixtures thereof, and a hydroxy carboxylic compound selected from non-toxic salts of hydroxy carboxylic acids, non-toxic salts of aluminum chelates of hydroxy carboxylic acids, codried mixtures of aluminum hydroxide with non-toxic salts of aluminum chelates of hydroxy carboxylic acids, and mixtures thereof. These compounds should be present in the complex in such amounts as to yield an Al/Zr mol ratio of about 10:1 to 1:10, and preferably about 1:1 to 4:1, and should be such as to yield a pH of at least about 3 when the complex is placed in aqueous solution in an amount such that the solution contains about 5 to 15 weight percent of zirconium plus aluminum, calculated as the oxides.

The astringent complexes of the present invention may be obtained in solution or dry powder form. As a result, the complexes are satisfactory for use in any of a wide variety of conventional anti-perspirant forms, including lotions, creams, roll-ons, sticks, aerosol sprays, and the presently popular powder-in-oil sprays.

DETAILED DESCRIPTION OF PREFERRED EMBODIMENTS

The basic aluminum compounds which may be used in forming the complexes of the present invention include the conventional basic aluminum salts which have been known to the anti-perspirant art for some time, and which have a degree of anti-perspirant efficacy in their own right, as a result of the presence of the active aluminum ion. These basic aluminum salts may be represented by the following general empirical formula:

$$Al_2(OH)_{6-nx}A_x$$

wherein x may vary from greater than 0 to less than 6, $6-nx$ is greater than or equal to 0, $n$ is the valence of A, and A is selected from the group consisting of halides, nitrate, sulfamate, sulfate and mixtures thereof.

It will of course be understood that the above formula is greatly simplified and is intended to represent and include basic aluminum compounds containing coordinated and/or bound molecules of water as well as polymers, complexes and mixtures of the above basic formula.

Particularly preferred basic aluminum compounds of the above formula are the two-thirds to five-sixths basic aluminum chlorides, in which A is chloride and x is between about 1 and 2 and need not be an integer. Thus, such basic aluminum chlorides may be represented by the formulas

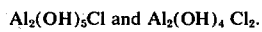

$$Al_2(OH)_5Cl \text{ and } Al_2(OH)_4Cl_2.$$

The basic aluminum chlorides are also referred to as aluminum chlorhydroxide or aluminum chlorhydrate or aluminum hydroxy chloride, and are commercially available from Reheis Chemical Company, Division of Armour Pharmaceutical Company under the trademark "Chlorhydrol".

In addition to the simple basic aluminum salts indicated above, complexes or derivatives of the basic aluminum salts may also be used advantageously in the complexes of the present invention. Examples of such derivatives or complexes include the phenolsulfonate derivatives described in U.S. Pat. No. 3,634,480 to Sheffield. Such complexes are formed by reacting five-sixths basic aluminum chloride with phenolsulfonic acid, zinc phenolsulfonate or aluminum phenolsulfonate. Other suitable derivatives and complexes of basic aluminum salts which may be used in the complexes of the present invention will be readily apparent to those of ordinary skill in the art in view of the present specification.

The zirconium compounds which are useful in forming the complexes of the present invention include both the zirconium oxy salts and zirconium hydroxy salts, also referred to as the zirconyl salts and zirconyl hydroxy salts. These compounds may be represented by the following general empirical formula:

$$ZrO(OH)_{2-nz} B_z$$

wherein z may vary from about 0.9 to 2 and need not be an integer, n is the valence of B, 2—nz is greater than or equal to 0, and B may be the same as A in the previous formula, that is B may be selected from the group consisting of halides, nitrate, sulfamate, sulfate and mixtures thereof. Although only zirconium compounds are exemplified in this specification, it will be understood that other Groups IV B metals, including hafnium could be used to form the complexes of the present invention.

As with the basic aluminum compounds, it will be understood that the above formula is greatly simplified and is intended to represent and include compounds having coordinated and/or bound water in various quantities, as well as polymers, mixtures and complexes of the above. As will be seen from the above formula, the zirconium hydroxy salts actually represent a range of compounds having various amounts of the hydroxyl group, varying from about 1.1 to only slightly greater than 0 groups per zirconium atom.

Particularly preferred zirconium for use in the present invention include zirconyl chloride (also referred to as basic zirconium chloride or zirconium oxy chloride) and zirconyl hydroxy chloride, which may be represented by the simple formulas $ZrO Cl_2$ and $ZrO(OH)Cl$, respectively. These compounds are commercially available in solution form. In the alternative, the zirconium compounds can be made by dissolution of commercially available zirconium carbonate paste (carbonated hydrous zirconia) in the appropriate amount of the acid of the anion to be used, e.g., hydrochloric acid. Other useful zirconium salts will be apparent to those of ordinary skill in the art, such as trioxodizirconium hydroxy halides and similar salts described, for example, in U.S. Pat. No. 2,837,400 to Blumenthal.

The particular hydroxy carboxylic compounds which may be used to form the complexes of the present invention include nontoxic salts of hydroxy carboxylic acids, non-toxic salts of aluminum chelates of hydroxy carboxylic acids, codried mixtures of aluminum hydroxide with non-toxic salts of aluminum chelates of hydroxy carboxylic acids, and mixtures thereof. It is believed that the salts of hydroxy carboxylic acids, even if insoluble in water, form complexes with the zirconium compounds and basic aluminum compounds, which complexes are soluble in water. Moreover, since the complexes of the present invention may be dried to a solid powder form, it is not necessary that the complexes be stable in aqueous solution for any great length of time, except when it is desired to redissolve the powder for use in solution form.

As used herein, the term "non-toxic salts" is intended to include those salts or compounds in which one or more non-toxic cations are reacted with hydroxy carboxylic acids and/or aluminum chelates of hydroxy carboxylic acids. The non-toxic cation may include the alkali metals, such as sodium, potassium and lithium, the alkaline-earth metals, such as magnesium and calcium, as well as zinc, zirconium, aluminum and ammonium.

Among the non-toxic salts which may be used to form the complexes of the present invention are those derived directly from hydroxy carboxylic acids. Suitable hydroxy carboxylic acids (also referred to as hydroxy acids) include the organic acids having a hydroxyl group alpha and/or beta to the carboxylic acid radical. Examples of such acids include lactic, citric, tartaric, glycolic, gluconic, trihydroxy glutaric, citryl trigluconic, citryl monogluconic, citryl digluconic, malic, tetrahydroxy adipic, and citramalic acids, and mixtures thereof. In general, the suitable hydroxy carboxylic acids are at least bidentate, and have a valence of from —1 to —4. It will be understood that the hydroxy carboxylic salts may contain either or both forms of the same ligand derived from the hydroxy carboxylic acid, one form corresponding to the form of the acid in which both the carboxyl and hydroxyl groups have been neutralized, and the other form corresponding to that form of the acid in which only the carboxyl groups have been neutralized, and whose hydroxyl group may be coordinated to a cation.

The non-toxic salts of hydroxy carboxylic acids may be obtained commercially or prepared by reacting the desired hydroxy carboxylic acid with the hydroxide, oxide, carbonate, or bicarbonate of the desired non-toxic cation. Such reaction may be carried out simply in aqueous solution in the appropriate stoichiometric amounts. Examples of suitable non-toxic salts of hydroxy carboxylic acids which may be used in forming the complexes of the present invention, and which are illustrated in the specific examples below, include sodium lactate, magnesium glycolate, potassium tartrate and calcium gluconate. Other suitable non-toxic salts of hydroxy carboxylic acids useful in the present invention will be evident to those of ordinary skill in the art in view of this specification.

In addition to the non-toxic salts derived directly from hydroxy carboxylic acids, the complexes of the present invention may also contain non-toxic salts derived from aluminum chelates of hydroxy carboxylic acids. These salts or compounds are described in detail in U.S. Pat. No. 3,553,316, issued January 5, 1971 to Rubino for "Anti-perspirant Compositions Containing Aluminum Chelates of Hydroxy Carboxylic Acids." The disclosure of U.S. Pat. No. 3,553,316 is incorporated herein by reference.

In general, as explained in more detail in U.S. Pat. No. 3,553,316, the non-toxic salts of aluminum chelates of hydroxy carboxylic acids may be formed by reacting the desired hydroxy carboxylic acid with an aluminum hydroxy compound and/or an aluminum halo-hydroxy compound to first chelate the aluminum.

The aluminum chelate is then reacted with an oxide, hydroxide or carbonate of the desired non-toxic cation. The same non-toxic cations and the same carboxylic acids as mentioned previously in connection with the direct salts of hydroxy carboxylic acids may be used in forming the salts of aluminum chelates of hydroxy carboxylic acids.

Instead of reacting the desired hydroxy carboxylic acid with an aluminum hydroxy compound, followed by reacting with an oxide, hydroxide or carbonate of the non-toxic cation, the salt of the aluminum chelate may be formed by refluxing an aqueous solution of the hydroxy carboxylic acid followed by reaction with the aluminate of the non-toxic cation.

With respect to the reaction of a hydroxy carboxylic acid with an aluminum halo-hydroxy compound, U.S. Pat. No. 3,553,316 only mentions aluminum chlorhydroxy compounds. However, it will be understood that other halides besides chloride may be used, including particularly the bromo hydroxy compounds.

In general, as described in U.S. Pat. No. 3,553,316, the salts of aluminum chelates useful in the present invention may be represented by the following formula:

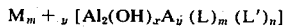

$$M_m +_y [Al_2(OH)_x A_y (L)_m (L')_n]$$

where A is halide, M represents one or more non-toxic cations, and L and L' are the two forms of the same ligand derived from the hydroxy carboxylic acid. L and L' are at least bidentate, and have a valence of between $-1$ to $-4$; L corresponds to that form of the acid in which both the carboxyl and hydroxyl groups have been neutralized, L' corresponds to that form of the acid in which only the carboxyl groups have been neutralized, and whose hydroxyl group is coordinated to an aluminum atom; where $y$, $m$, $n$, and $x$ are numbers whose sum is such as to balance the positive valences of the cation M, and aluminum; $m + y$ is the total number of gram atoms of the cation M; and $m + n$ is the total number of gram molecular weights of alpha- or beta-hydroxy aliphatic carboxylic acid. It is to be understood that in some chelates, only L is present; in other chelates only L' is present; and in still other chelates L and L' are present.

In the case of the use of aluminum hydroxy compounds or aluminates as the aluminum source, namely when $y$ is 0 (halide atoms being absent), the total number of gram atoms of cation or cations will be represented as the sum of $m + n$, and the chelate will have the following empirical formula:

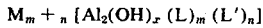

$$M_m +_n [Al_2(OH)_x (L)_m (L')_n]$$

where M, L and L' are as above; where $m$, $n$, and $x$ are numbers whose sum is such as to balance the positive valences of the cation M, and aluminum, $m + n$ is the total number of gram atoms of the cation M, and $m + n$ is the total number of gram molecular weights of alpha- or beta-hydroxy aliphatic carboxylic acid.

In the above formulas, it will be understood that the numbers representing $y$, $m$, $n$, and $x$ need not be integers, but may be fractional quantities. Also, it will be understood that the ranges of values of $x$, $y$, $m$, and $n$ will vary depending upon whether the chelation is bidentate, tridentate, or tetradentate.

Examples of suitable non-toxic salts of aluminum chelates of hydroxy carboxylic acids which may be used in the present invention, and which are illustrated in the specific examples below, include potassium aluminum chlorhydroxy gluconate, calcium aluminum chlorhydroxy lactate, magnesium aluminum chlorhydroxy citrate, magnesium aluminum hydroxy glycolate, calcium aluminum bromo hydroxy lactate, magnesium aluminum bromo hydroxy glycolate, sodium aluminum hydroxy citrate, zinc aluminum bromo hydroxy lactate, calcium aluminum hydroxy citryl trigluconate, magnesium aluminum hydroxy gluconate, and others which will be evident to those of ordinary skill in the art in view of this specification. Other non-toxic salts of aluminum chelates of hydroxy carboxylic acids which may be used in the present invention are described in U.S. Pat. No. 3,200,136 to Grossmith.

Particularly preferred salts of aluminum chelates of hydroxy carboxylic acids useful in forming the complexes of the present invention include sodium aluminum hydroxy lactate, available from Reheis Chemical Company division of Armour Pharmaceutical Company under the name of "Nalac", and sodium aluminum chlorhydroxy lactate, available from Reheis under the trademark "Chloracel".

In addition to the non-toxic salts of aluminum chelates of hydroxy carboxylic acids per se, codried mixtures of such salts of aluminum chelates with aluminum hydroxide may also be used in forming the complexes of the present invention. Such codried mixtures are known for use as antacids and are described in detail in U.S. Pat. No. 3,499,963, issued Mar. 10, 1970 to Rubino for "Codried Aluminum Hydroxide-Aluminum Chelate Antacid". The disclosure of U.S. Pat. No. 3,499,963 is incorporated herein by reference.

The codried antacid mixtures may be prepared by mixing aluminum hydroxide gel with any of the non-toxic salts of aluminum chelates of hydroxy carboxylic acids described above and in U.S. Pat. No. 3,553,316. As explained in detail at column 7 of U.S. Pat. No. 3,499,963, the order and method of mixing are not particularly critical, but the aluminum hydroxide and chelate salt should be mixed in the presence of water, for example in a solution of the chelate, or a slurry of the aluminum hydroxide gel. The resulting mixture may be dried in any convenient manner to form a codried gel or powder. The weight ratio of aluminum hydroxide to chelate salt may vary from about 0.3 to 1 to about 1.5 to 1, as the antacids of the patent, or may vary outside that range if desired to adjust the pH.

The particular amounts of each of the compounds to be added to form the complexes of the present invention may vary over a large range, depending upon the particular properties desired.

In general, the relative amounts of basic aluminum compound and zirconium compound to be added should be such as to yield an Al/Zr mol ratio of between about 10:1 and 1:10, and preferably about 1:1 to 4:1. Although greater amounts of zirconium would be desirable in the complex from the standpoint of antiperspirant efficacy, it will be appreciated that zirconium is considerably more expensive than aluminum. In addition, the greater the amounts of zirconium in the complex, the greater the chance of skin irritation, and the greater the amount of the hydroxy carboxylic compound which must be added to obtain a satisfactory pH.

The amount of the hydroxy carboxylic compound to be added will also vary greatly depending upon the Al/Zr ratio, the particular hydroxy carboxylic compound used, and the pH range which is desired for the particular astringent complex. In general, sufficient hydroxy carboxylic compound should be added so that the pH of an aqueous solution of the complex at the normal concentrations for anti-perspirant use will be at least about 3, and preferably in the range of about 3 to 5. The usual concentration of the complexes of the present invention for anti-perspirant use will be such that a solution contains a total aluminum plus zirconium concentration of about 5 to 15 weight percent, with the aluminum and zirconium being calculated as the oxides (i.e., $ZrO_2$ and $Al_2O_3$).

If desired, the pH or the concentration of aluminum in the complexes of the present invention may be adjusted by adding aluminum chloride ($AlCl_3$) to the reaction mixture in the formation of the complexes of the present invention. Aluminum chloride, although quite acidic in solution, is well known for its anti-perspirant efficacy.

Among the advantages of the complexes of the present invention is that they are more basic and better buffers than the simple amino acid complexes previously used. This is due to the fact that most of the derivatives of alkali and alkaline earth metals are hydroxylated. Since the formation of complexes of the present invention results in increasing the pH of the highly acid zirconium systems, they can be used in smaller amounts than the simple amino acids to achieve the necessary pH levels for anti-perspirant use. In addition other ions known for their anti-perspirant activity as well as their basic character are introduced into the astringent complexes of the present invention. For example, the use of aluminum chelates and codried mixtures including aluminum hydroxide results in the addition of more aluminum which is well known for its anti-perspirant activity. Furthermore, the presence of the "sequestering" hydroxy-acid moieties confers an enhanced stability upon the very weakly basic zirconium ion in the process of buffering its solutions to more alkaline pH levels.

The method of forming the complexes of the present invention is not particularly critical. In general, the complexes may be formed simply by adding the various components together in an aqueous solution and then, if desired, drying the solution to a dry powder. The various components are preferably added one at a time with stirring or agitation. Moderate heating, such as to a maximum of about 75° or 85° C. for up to a half hour may be advantageous after addition of certain ingredients, particularly when an insoluble compound is added or when a precipitate is formed after the addition of an ingredient. Where a water insoluble hydroxy carboxylic compound is being used, it is preferable to add this last.

The drying step is not particularly critical and may be carried out in a number of different ways, including vacuum drying, oven drying, spray drying or freeze drying. It will be understood that drying does not mean that all of the water is removed, since a certain amount of water should remain in the complex as coordinated and/or bound water. Thus, drying to just past the point where the solution becomes friable solid should be sufficient. If the complex is over dried, so that some of the coordinated and/or bound water is removed, the stability and/or activity of the complex may be interferred with, and the complex may not be readily redissolvable in solvents, particularly hydroalcoholic solvents.

While it has been indicated that the reaction process is not considered particularly critical, it will be understood that sufficient time, heat and agitation are needed to allow reaction of the salts to form the new complexes of the present invention. This is particularly so in the case of insoluble hydroxy carboxylic compounds which may be used to form complexes of this invention. Although I do not wish to be bound by any particular theory, it is believed that there is a continuation of the reaction during the drying of the solution to a solid powder. Thus, the pH of a reconstituted solution is often higher than might otherwise be expected from the pH of the solution before drying, even taking into consideration different solution concentrations.

The complexes of the present invention will now be illustrated in more detail with reference to the following specific, non-limiting examples:

EXAMPLE I

A sodium lactate buffer solution was prepared by mixing 204 g of 88% by weight lactic acid solution with 160 g of 50% by weight sodium hydroxide. To 200 g of 50% by weight 5/6 basic aluminum chloride (12% Al) was added 62.3 g of zirconyl hydroxychloride (14.1% Zr) and 7 g of the sodium lactate buffer. The buffered aluminum zirconium system was then dried at 50° C. under a vacuum of 300 mm Hg yielding a friable solid containing 19.9% Al, 7.8% Zr, 2.2% Na, and 4.90% lactic acid with an Al:Zr mole ratio corresponding to 8.6:1. This solid was reconstituted in water to 20% by weight solids and the resulting solution exhibited a pH of 4.1.

EXAMPLE II

The same buffer and other reagents as described in Example I were employed, but at different levels. To 10 g of 5/6 basic aluminum chloride was added 122 g of zirconyl hydroxychloride and 30 g of sodium lactate buffer followed by drying the resulting solution as in Example I. The friable solid obtained analyzed: 1.9% Al, 30.6% Zr, 7.1% Na, and 23.3% lactic acid with an Al:Zr mole ratio of 1:4.8. This solid was reconstituted in water to a 20% by weight solids level and the resulting clear solution was found to display a pH of 3.4.

EXAMPLE III

A magnesium glycolate buffer was prepared by reacting at 70° C., 20 g of $MgCO_3$ (26.3% Mg) with 65.4 g of 70% glycolic acid, followed by the addition of 200 mls of water. To this buffer was then added 200 g of 5/6 basic aluminum chloride (12% Al) and 112 g of zirconyl chloride (13.3% Zr). The product was then dried as in Example I to a friable solid, analyzing: 12.8% Al, 8.09% Zr, 2.81% Mg, and 24.2% glycolic acid. The product had an Al:Zr mole ratio of 5.34:1 and when reconstituted in water to 20% by weight solids, displayed a pH of 3.7.

EXAMPLE IV

A potassium tartrate buffer was prepared by mixing KOH with tartaric acid at a K:tartaric acid mole ratio of 2:1 and diluting the resulting compound with enough water to yield a buffer solution with a pH of 2.9. 73 g of the buffer was then added to a reconstituted (30% by weight) dried zirconyl chloride five-sixths basic aluminum chloride solution prepared at a mole ratio of Al:Zr of 4:1. This buffered solution was re-dried as in Example I, and analyzed: 12.9% Al, 11.2% Zr, 7.9% K, and 14.6% tartaric acid. The re-dried product was reconstituted to 20% by weight in water and exhibited a pH of 3.8.

EXAMPLE V

To 100 g of 50% Chlorhydrol (trademark of Reheis Chemical Company for 5/6 basic aluminum chloride) solution (12.8% Al) was added with agitation 100 g of 33.3% by weight water solution of zirconyl hydroxychloride (14.2% Zr) and 230 g of water. To this solution was then added 35 g of Nalac (product of Reheis Chemical Company for sodium aluminum hydroxy lactate) containing 2.9% by weight aluminum. The solution was then dried as in Example I to a friable solid that analyzed: 15.6% Zr, 14.7% Al, 8.71% lactic acid and 2.0% Na. The solid product was water soluble to at least 20% by weight and at this concentration displayed a pH of 3.8.

EXAMPLE VI

To 100 g of 5/6 basic aluminum bromide (11.1% Al) was added 64.6 g of zirconyl hydroxybromide (14.5% Zr) and 7.5 g of $Ca(C_6H_{11}O_7)_2$ (USP calcium gluconate obtained from Merck & Co.) in 300 g of water. The reaction was carried out at 50° C. for 30 minutes under agitation, resulting in a water clear product. This product was dried as in Example I and was found to be soluble to 20% by weight in water imparting a pH to the water of 3.7. The dried product analyzed: 12.2% Al, 9.41% Zr, 0.72% Ca, and 27.9% Br with an Al:Zr mole ratio of 4.4:1.

EXAMPLE VII

A buffer was prepared by reacting 62.9 g of 50% Chlorhydrol with 102.8 g of glucono -delta- lactone slurried in 35 g of water. The resulting solution was heated with agitation at 55° C. for 2 hours followed by the addition of 67 g of potassium hydroxide (50% solution), causing the system to exhibit a pH of 7.1, while containing 2.7% Al.

To 100 g of a basic aluminum chloride - basic aluminum sulfate couple $[Al_9(OH)_{23}Cl_2SO_4]$ (3% Al) was added 234 g of zirconyl bromide (17.11% Zr) and 200 g of the above buffer. The product was dried as in Example I to a friable solid soluble to at least 20% by weight in water. The 20% by weight solids in water solution had a pH equal to 3.5. The dried product analyzed: 3.5% Al, 13.0% Zr, 12.1% Cl, 1.9% Br, and 8.3% K.

EXAMPLE VIII

A complex buffer was prepared by reacting with agitation, 122 g of 5/6 basic aluminum chloride (12.0% aluminum) with 62 g of 88 percent by weight lactic acid in 55 g of water for 2 hours at 60° C. To this hot solution was then added over a period of 1 hour, 20 g of USP $CaCO_3$ until all the $CO_2$ was evolved and the solution became clear. The buffer contained 4.0% Al.

To 25 g of the above buffer was then added 8.5 additional g of 5/6 basic aluminum chloride (12% Al) and 200 g of zirconyl hydroxychloride (14.1% Zr). The resulting system was water clear and was then dried at 50° C. and under a vacuum of 300 mm Hg. The resulting dried product analyzed: 4.1% Al, 31.4% Zr, 14.9% Cl, 0.78% Ca, and 10.3% lactic acid and had an Al:Zr mole ratio of 1:2.3. The dried product was reconstituted in water to 20% by weight. The resulting solution's pH was determined to be 3.4.

EXAMPLE IX

A buffer was prepared by reacting with agitation, 56.8 g of Chlorhydrol 50% solution with 98 g of water and 55.0 g of citric acid monohydrate for 2 hours at 55° C. To this hot solution was then added 30 g of $MgCO_3$ (26.3% Mg) maintaining heat and agitation until complete clarity was observed. The buffer contained 2.3% Al.

To 50 g of this buffer was added 67.8 g of 50% Chlorhydrol (12.0% Al) and 40 g of zirconyl chloride (13.6% Zr). The resulting clear solution was dried as in Example VIII to a solid analyzing: 14.0% Al, 8.3% Zr, 16.4% Cl, 2.4% Mg, and 13.9% citric acid with an Al:Zr mole ratio of 5.7:1. When the solid product was reconstituted in water to a 20% by weight solution, the resulting pH of this solution was measured to be 3.7.

EXAMPLE X

A complex buffer was prepared by adding to 110 g of 70% glycolic acid 20 g of dried USP aluminum hydroxide gel (54.3% $Al_2O_3$) until clarity was reached through agitating and heating the solution to 50° C. for several minutes. To the resulting clear solution was then added 10 g of $MgCO_3$ (26.3% Mg) until clarity was again observed. This buffer contained 2.0% Al.

To 192 g of 5/6 basic aluminum chloride (12.0% Al) was added 50 g of the above buffer and 103 g of zirconyl chloride (13.6% Zr) and 50 g of water. The resulting clear solution was dried as in Example VIII to a friable solid, when then reconstituted in water to 20% by weight exhibited a pH of 3.9. The dried product analyzed: 15.6% Al, 8.9% Zr, 17.6% Cl, 0.34% Mg and 5.6% glycolic acid with an Al:Zr mole ratio of 6:1.

EXAMPLE XI

A buffer was prepared by reacting 112 g of 88% by weight lactic acid with 138 g of 5/6 basic aluminum bromide (10% Al) and 50 mls. of water. The mixture was heated for three hours at 60° C., while being agitated. To this solution was then added $CaCO_3$ (USP) until a pH of 3.6 was obtained at room temperature and the resulting clear solution contained 3.6% Al.

To 457 g of zirconyl hydroxychloride (14.1% Zr) was added 10 g of 5/6 basic aluminum chloride (12.0% Al) and 60 g of the above described buffer followed by drying as in Example VIII. The dried product when reconstituted in water to 20% by weight had a pH of 3.3 and analyzed 4.0% Al, 27.2% Zr, 1.0% Ca, 0.14% Br, 13.1% Cl, and 20.3% lactic acid.

EXAMPLE XII

A complex buffer was prepared by reacting 174.4 g of five-sixths basic aluminum bromide (10% Al) with 183 g of 70% glycolic acid under agitation at 60° C. for 2 hours. To this solution was then added $MgCO_3$ (26.3% Mg) to obtain a buffer at a pH of 3.1 and containing 2.6% Al.

To 50 g of 50% Chlorhydrol was then added 50 g of the above buffer and 47.3 g of zirconyl chloride (13.3% Zr). The resulting clear solution was dried as in Example VIII to a solid, which when reconstituted in water to 20 weight percent gave a clear solution with a pH of 3.7. The solid analyzed: 11.0% Al, 9.8% Zr, 1.0% Mg, 0.92% Br, 15.4% Cl and 15.1% glycolic acid with an Al:Zr mole ratio of 3.5:1.

EXAMPLE XIII

A buffer was prepared by reacting 80.2 of glucono-delta-lactone and 31.5 g of citric acid mono hydrate in 125 g of water, which was allowed to stand for 16 hours while being agitated. To this solution was then added 33 g of $MgCO_3$ (26.3% Mg) while maintaining the system at 50° C. The resulting clear solution constituted the buffer which was added in toto to a mixture of 10 g of 5/6 basic aluminum chloride (12% Al) and 182 g of zirconyl hydroxychloride (14.1% Zr). The resulting solution was dried as in Example VIII and analyzed: 0.35% Al, 7.3% Zr, 6.1% Mg, and 65.8% citryl trigluconic acid with an Al:Zr mole ratio of 1:6.2. The pH of a reconstituted solution containing 20% by weight of dried product was 3.5.

EXAMPLE XIV

A buffer was prepared by refluxing for 2 hours with agitation, 63 g of citric monohydrate dissolved in 240 g of water to which was added a sodium aluminate solution prepared by dissolving 33.9 g of sodium aluminate in 300 g of water. The resulting buffer contained 0.92% aluminum.

To 20 g of the above buffer was added 100 g of five-sixths basic aluminum bromide (11.1% Al) and 26.3 g of zirconyl hydroxybromide (14.5% Zr). The resulting product was clear and was dried as in Example VIII to a solid analyzing 16.8% Al, 6.05% Zr, 0.40% Na, 31.5% Br and 3.1% citric acid with an Al:Zr mole ratio of 9.8:1. The solid when dissolved in water to 20 weight percent resulted in a clear liquid with a pH of 3.9.

EXAMPLE XV

A complex buffer was prepared by adding to 218 g of five-sixths basic aluminum bromide (11.1% Al) 155 g of 88% lactic acid and 135 g of water. The reaction mixture was heated to 70° C. for 2 hours with agitation. To the resulting clear solution was added 40.5 g of reagent zinc oxide which required agitation for clarity to re-occur. This clear solution contained 4.3% Al.

To 25 g of the above buffer, was added 25 g of 5/6 basic aluminum bromide (11.1% Al) and 297 g of zirconyl hydroxybromide (14.5% Zr). The product was dried as in Example VIII resulting in a product analyzing: 2.0% Al, 25.6% Zr, 1.5% Zn, 4.7% lactic acid and 26.3% Br with an Al:Zr mole ratio of 1:3.8. The dried product when redissolved to 20% by weight in water, imparted a pH of 3.5 to the solution.

EXAMPLE XVI

A buffer was prepared by dissolving 200.8 g of glucono-delta-lactone in 84 g of water. To this was then added 56 grams of dried USP $Al(OH)_3$ gel (54.3% $Al_2O_3$). The reaction mixture required 2 hours of agitation at 50° C. for the system to become water clear. The buffer contained 2.9% Al.

To 100 g of 5/6 basic aluminum bromide (11.1% Al) was added 100 g of the above buffer and 84 g of zirconyl hydroxybromide (14.5% Zr). The resulting clear solution was dried as in Example VIII to a solid analyzing 9.82% Al and 7.08% Zr, which corresponds to an Al:Zr mole ratio of 4.6:1. The product was water soluble. When it was dissolved to 20% by weight in water, the resulting solution had a pH of 3.5.

EXAMPLE XVII

A buffer was prepared by reacting 31.5 g of citric acid monohydrate with 80.2 of glucono-delta-lactone and 150 g of water under reflux conditions with agitation for 4 hours. To this solution was then added 20 g of USP $CaCO_3$ and 10 g of dried aluminum hydroxide gel (54.3% $Al_2O_3$). The resulting clear solution contained 1.02% Al.

To 100 g of 50% Chlorhydrol solution (12% Al) was added 50 g of zirconyl hydroxychloride (14.1% Zr) and 50 g of the above buffer. The resulting clear product was dried as in Example VIII to a solid containing 14.9% Al and 6.43% Zr with an Al:Zr mole ratio of 7.9:1. The solid was redissolved in water to 20 weight percent. A 20% by weight solution of the dried product had a pH of 3.7.

EXAMPLE XVIII

A buffer was prepared by reacting 89.1 g of glucono-delta-lactone, 50 g of water, and 12.8 g of USP dried aluminum hydroxide gel (54.3% $Al_2O_3$) for two hours at 50° C. under agitation. To this solution was then added 20 g of $MgCO_3$ (26.3% Mg) with heating and agitation being maintained until the resulting buffer became water clear. The buffer contained 1.5% Al.

To 100 g of 50% Chlorhydrol was added 50 g of zirconyl hydroxychloride (14.1% Zr) and 27 g of the above buffer. The resulting liquid product was dried as in Example VIII, and found to contain 15.4% Al and 6.2% Zr with an Al:Zr mole ratio of 8.3:1. The dried product was redissolved in water and displayed a pH of 4.1 at 20% by weight.

EXAMPLE XIX 0.2 parts/wt. of $Al(OH)_3$ Na Al chlorhydroxy lactate buffer prepared as per U.S. Pat. 3,499,963 were added to 41.6 parts/wt. of $ZrOCl_2$ solution containing 13.2% Zr - causing a rise in pH from ∼ 0 to 0.25. This buffered solution was then slowly added to 60.9 parts/wt. of aluminum chlorhydrate $[Al_2(OH)_5Cl]$ solution containing 2.68% Al. A water white solution with a pH = 2.6 was obtained, which was then oven-drived at 65°/C. for 48 hours.

A light yellow crystalline solid was obtained, yielding the following assay: Al=7.2%, Zr=24.9%, Al:Zr::1.07:1.0, Na=0.14%, lactic acid=0.63%. A reconstituted 15% aqueous solution was viscous, slightly cloudly and had a pH of 3.6.

EXAMPLE XX 0.3 parts/wt. of $Al(OH)_3MgAl$ hydroxy digluconate buffer prepared as per U.S. Pat. 3,499,963 were added to 27.4 parts/wt. of $ZrO(OH)Cl$ solution containing 13.3% Zr — causing a rise in pH from 0.45 to 0.6. This buffered solution was then added to 85.2 parts/wt. of aluminum chlorhydrate $[Al_2(OH)_5Cl]$ solution containing 2.68% Al. A slightly hazy solution with a pH = 3.3 was obtained, which was oven-drived at 65°/C. for 30 hours.

A light yellow crystalline solid was obtained, yielding the following assay: Al = 14.8%, Zr = 15.1%, Al:Zr::3.3:1.0, Mg=0.04%. A reconstituted 15% aqueous solution was slightly cloudy and had a pH of 4.1.

EXAMPLE XXI 0.2 parts/wt. of $Al(OH)_3NaAl$ hydroxy lactate buffer prepared as per U.S. Patent 3,499,963 were added to 20.4 parts/wt. of ZrO(OH)Cl solution containing 13.3% Zr — causing a rise in pH from 0.45 to 1.01. This buffered solution was then slowly added to 81.4 parts/wt. of aluminum chlorhydrate [$Al_2(OH)_5Cl$] solution containing 3.86% Al. A slightly turbid solution with a pH = 3.6 was obtained, which was then oven-dried at 65°/C. for 40 hours.

A yellow crystalline solid was obtained, yielding the following asay: Al = 16.9%, Zr = 14.6%, Al:Zr::3.9:1.0, Na = 0.14%, lactic acid = 0.53%. A reconstituted 15% aqueous solution was slightly cloudy and had a pH of 4.15.

EXAMPLE XXII 0.2 parts/wt. of Al(OH)$_3$NaAl hydroxy lactate buffer prepared as per U.S. Pat. 3,499,963 were added to 13.8 parts/wt. of $ZrOCl_2$ solution containing 13.2% Zr-causing a rise in pH from 0 to 0.1. This buffered solution was then slowly added to 77.8 parts/wt. of aluminum chlorhydrate [$Al_2(OH)_5Cl$] solution containing 3.84% Al. A slightly turbid solution with a pH = 3.4 was obtained, which was then oven-dried at 65°/C. for 48 hours.

A yellow crystalline solid was obtained, yielding the following assay: Al = 13.4%, Zr = 10.2%, Al:Zr::4.45:1.0, Na = 0.2%, lactic acid = 1.1%. A reconstituted 15% aqueous solution was slightly cloudy and had a pH of 4.9.

EXAMPLE XXIII 0.2 parts/wt. of Al(OH)$_3$MgAl hydroxy gluconate buffer prepared as per U.S. Pat. 3,499,963 were added to 24.0 parts/wt. of $ZrOCl_2$ solution containing 13.2% Zr — causing a rise in pH from ~ 0 to 0.2. This buffered solution was then slowly added to 30.7 parts/wt. of aluminum chlorhydrate [$Al_2(OH)_5Cl$] solution containing 2.64% Al. A water white solution with a pH = 2.4 was obtained, which was then oven-dried at 65°/C. for 48 hours.

A yellow crystalline solid was obtained, yielding the following assay: Al = 7.6%, Zr = 24.2%, Al:Zr::1.04:1.0, Mg = 0.02%. A reconstituted 15% aqueous solution was cloudy and gellatinous, and had a pH of 3.5.

EXAMPLE XXIV 0.2 parts/wt. of Al(OH)$_3$MgAl hydroxy tartrate buffer prepared as per U.S. Pat. 3,499,963 were added to 16.6 parts/wt. of $ZrOCl_2$ solution containing 13.2% Zr — causing a rise in pH from ~ 0 to pH 0.1. This buffered solution was then slowly added to 79.4 parts/wt. of aluminum chlorhydrate [$Al_2(OH)_5Cl$] solution containing 4.14% Al. A cloudy solution with a pH 3.4 was obtained, which was then oven-dried at 65°/C. for 48 hours.

A yellow crystalline solid was obtained, yielding the following assay: Al = 17.6%, Zr = 11.1% [Al:Zr::5.4:1.0] Mg = 0.02%. A reconstituted 15% aqueous solution was very slightly cloudy and had a pH of 4.0.

EXAMPLE XXV 0.2 parts/wt. of Al(OH)$_3$Al dihydroxy gluconate buffer prepared as per U.S. Pat. 3,499,963 were added to 27.4 parts/wt. of ZrO(OH)Cl solution containing 13.3% Zr — causing a rise in pH from 0.45 to 0.70. This buffered solution was then slowly added to 86.1 parts/wt. of aluminum chlorhydrate [$Al_2(OH)_5Cl$] solution containing 3.76% Al. A slightly turbid solution with a pH = 3.6 was obtained, which was then oven-dried at 65°/C. for 48 hours.

A light yellow green crystalline solid was obtained, yielding the following assay: Al = 15.4%, Zr = 17.2%, Al:Zr::3.0:1.0. A reconstituted 15% aqueous solution was slightly turbid and had a pH of 4.15.

EXAMPLE XXVI 0.2 parts/wt. of Al(OH)$_3$K bihydroxy gluconate buffer prepared as per U.S. Pat. 3,499,963 were added to 13.8 parts/wt. of $ZrOCl_2$ solution containing 13.2% Zr — causing a rise in pH from ~ 0 to 0.1. This buffered solution was then slowly added to 77.7 parts/wt. of aluminum chlorhydrate [$Al_2(OH)_5Cl$] solution containing 4.03% Al. A slightly turbid solution with a pH = 3.7 was obtained, which was then oven-dried at 65°/C. for 48 hours.

A light yellow crystalline solid was obtained, yielding the following assay: Al = 17.6%, Zr = 9.9%, Al:Zr::6.0:1.0 K = 0.04%. A reconstituted 15% aqueous solution was slightly turbid and had a pH of 4.0.

EXAMPLE XXVII 0.5 parts/wt. of Al(OH)$_3$Mg gluconate buffer prepared as per U.S. Patent 3,499,963 were added to 27.6 parts/wt. of $ZrOCl_2$ solution containing 13.2% Zr — causing a rise in pH from ~ 0 to 0.4. This buffered solution was then slowly added to 87.0 parts/wt. of aluminum chlorhydrate [$Al_2(OH)_5Cl$] solution containing 3.7% Al. A slightly turbid solution with a pH = 3.4 was obtained, which was then oven-dried at 65°/C. for 48 hours.

A yellow crystalline solid was obtained, yielding the following assay: Al = 14.0%, Zr = 15.0%, Al:Zr::3.1:1.0 Mg = 0.1%. A 15% aqueous solution was slightly turbid and had a pH of 3.55.

EXAMPLE XXVIII 0.2 parts/wt. of $Al_2(OH)_3$Ca lactate buffer prepared as per U.S. Pat. No. 3,499,963 were added to 27.4 parts/wt. of $ZrOCl_2$ solution containing 13.2% Zr — causing a rise in pH from ~ 0 to 0.1. This buffered solution was then slowly added to 86.1 parts/wt. of aluminum chlorhydrate [$Al_2(OH)_5Cl$] solution containing 3.75% Al. A slightly cloudy solution with a pH = 2.9 was obtained, which was then oven-dried at 65°/C. for 48 hours.

A yellow crystalline solid was obtained, yielding the following assay: Al = 13.6%, Zr = 15.1%, Al:Zr::3.0:1.0,Ca = 0.1%. A reconstituted 15% aqueous solution was cloudy and had a pH of 3.1.

EXAMPLE XXIX 0.2 parts/wt. of Al(OH)$_3$MgAl hydroxy maleate buffer prepared as per U.S. Pat. 3,499,963 were added to 41.6 parts/wt. of $ZrOCl_2$ solution containing 13.2% Zr — causing a rise in pH from ~ 0 to 0.1. This buffered solution was then slowly added to 61.4 parts/wt. of aluminum chlorhydrate [$Al_2(OH)_5Cl$] solution containing 2.65% Al. A slightly cloudy solution with a pH = 1.3 was obtained, which was then oven-dried at 65°/C. for 48 hours.

A light yellow powder was obtained, yielding the following assay: Al = 8.0%, Zr = 26.0%, Al:Zr::1.0:1.0, Mg = 0.03%. A reconstituted 15% aqueous solution was cloudy and had a pH of 3.4.

EXAMPLE XXX 0.2 parts/wt. of $Al(OH)_3CaAl$ hydroxy gluconate buffer prepared as per U.S. Pat. 3,499,963 were added to 20.4 parts/wt. of $ZrO(OH)Cl$ solution containing 13.3% Zr — causing a rise in pH from 0.45 to 0.70. This buffered solution was then slowly added to 83.0 parts/wt. of aluminum chlorhydrate [$Al_2(OH)_5Cl$] solution containing 3.9% Al. A slightly cloudy solution with a pH = 3.6 was obtained, which was then oven-dried at 65°/C. for 48 hours.

A light yellow crystalline solid was obtained, yielding the following assay: Al = 15.7%, Zr = 13.0%, Al:Zr::4.1:1.0, Ca = 0.06%. A reconstituted 15% aqueous solution was slightly turbid and had a pH of 3.7.

EXAMPLE XXXI 0.2 parts/wt. of $Al(OH)_3KAl$ hydroxy citrate buffer prepared as per U.S. Pat. 3,499,963 were added 23.9 parts/wt. of $ZrOCl_2$ solution containing 13.2% Zr causing a rise in pH from ~ 0 to 0.1. This buffered solution was then slowly added to 30.7 parts/wt. of aluminum chlorhydrate [$Al_2(OH)_5Cl$] solution containing 2.65% Al. A slightly cloudy solution with a pH = 2.5 was obtained, which was then oven-dried at 65°/C. for 48 hours.

A yellow crystalline solid was obtained, yielding the following assay: Al = 7.6%, Zr = 24.2% Al:Zr::1.1:1.0. A reconstituted 15% aqueous solution was turbid and had a pH of 3.5.

As indicated previously, the complexes of the present invention may be used in a variety of conventional anti-perspirant forms which are applied to the human axilla for effective perspiration inhibition. In such formulations, the complex should be present in such amounts that the total aluminum plus zirconium content of the formulation is between about 1.5 and 15 weight percent (depending on the type of formulation employed), calculated as the oxides of the aluminum and zirconium.

For example, aqueous solutions of the complexes may be used in lotions, oil/water creams, and co-dispensing aerosols. The complexes of the present invention are not as a rule soluble in pure alcoholic solvent systems. However, the complexes may be considered for use in hydro-alcoholic solvents, the complexes of the present invention should be present in the above anti-perspirant forms in amounts such that the total content of aluminum plus zirconium in the formulation is on the order of about 5 to 15 weight percent (calculated as the oxides of aluminum and zirconium) or 10 to 30 weight percent of the active ingredient (calculated on a solids basis).

The complexes of the present invention may also be used in the now popular powder-in-oil aerosol sprays. The powder-in oil systems comprise the dispersion of a finely divided antiperspirant powder, such as the dried complexes of the present invention, in a non-solubilizing polar organic liquid such as an ester which serves as both a dispersion medium as well as an emollient. The organic liquid coats or wets the powder particles to render them heavier and more occlusive and/or substantive to the axillary region. This primary powder-in-oil suspension, known as the "concentrate", may also include a suspending or anti-compaction agent such as Cab-O-Sil or Bentone 34, to inhibit the dispersed phase from settling and compacting irreversibly. The so-called "extra-dry" formulations use less emollient and higher levels of dry powder, such as talc. Finally, after dynamic agitation the viscous concentrate is generally mixed with about 9 times its weight of a blend of standard propellants.

When used in the powder-in-oil aerosol sprays, the complexes of the present invention should be present in the finished formulation to the extent of about 1 to 6 weight percent, and preferably about 1.5 to 3 weight percent, total aluminum plus zirconium, calculated as the oxides. A typical powder-in-oil aerosol suspension would employ about 5 percent w/w of the active ingredient (dried complex) or about 2.5 percent total oxides.

Typical anti-perspirant formulations employing the complexes of the present invention are exemplified in Table I.

The present invention may be embodied in other specific forms without departing from the spirit or essential attributes thereof and, accordingly, reference should be made to the appended claims, rather than to the foregoing specification as indicating the scope of the invention.

TABLE I

ANTIPERSPIRANT FORMULATIONS

| Ingredient | A* Powder-in-oil aerosol | B* Powder in-oil extra-dry aerosol | C Spray: (Manual-Pump) | D Oil-in-water Lotion | E Oil-in-water cream |
|---|---|---|---|---|---|
| Active Ingredient (Antiperspirant) | | | | | |
| Complex of Example I | 3.5 | | | | |
| Complex of Example V | | | 10.0 | | |
| Complex of Example XII | | 5.0 | | | |
| Complex of Example IX | | | | 18.0 | 15.0 |
| Isopropyl Myristate | 6.0 | 3.0 | | | |
| Cab-O-Sil M-5 (1) | 0.3 | 0.5 | | | |
| Perfume | 0.2 | | 0.5 | q.s. | q.s. |
| Propylene Glycol | | | 15.0 | | |
| Propellant 11 (trichlorofluoromethane) | 45.0 | 45.0 | | | |
| Propellant 12 (dichlorodifluoromethane) | 45.0 | 45.0 | | | |
| Water | | | 19.5 | 66.0 | 56.0 |
| Alcohol SD-39C | | | 55.0 | | |
| Talc, U.S.P. | | 1.5 | | | |
| Arlacel 165 (4) | | | | | 18.0 |
| Amerchol L-101 (2) | | | | 5.0 | |
| Solulan 98 (2) | | | | 2.0 | |
| Myrj 52 (4) | | | | 4.0 | |

TABLE I-continued

ANTIPERSPIRANT FORMULATIONS

| Ingredient | A* Powder-in-oil aerosol | B* Powder in-oil extra-dry aerosol | C Spray: (Manual-Pump) | D Oil-in-water Lotion | E Oil-in-water cream |
|---|---|---|---|---|---|
| | Parts by Weight | | | | |
| Cetyl Alcohol | | | | 2.0 | |
| Glycerin | | | | 2.0 | 5.0 |
| Veegum HV (3) | | | | 1.0 | |
| Preservative | | | | q.s. | q.s. |
| Spermaceti | | | | | 5.0 |
| Titanium Dioxide | | | | | 1.0 |

(1) Cab-O-Sil M-5 - fumed amorphous silica of Cabot Corp.
(2) Amerchol L-101 and Solulan 98 - lanolin derivatives of Amerchol, Inc.
(3) Veegum HV - product of R. T. Vanderbilt & Co.
(4) Arlacel 165 and Myrj 52 - non-ionic emulsifiers of ICI America.
*For "powder-in-oil" aerosols, active ingredient powders are ground in a micronizer before use to yield powders containing a particle size greater than 97% through a 325 mesh screen (44μ).

I claim:

1. An astringent, water soluble complex formed by reacting in an aqueous solution:
   a. a basic aluminum compound selected from the group having the general empirical formula:

$Al_2(OH)_{6-nx}A_x$ 

wherein $x$ may vary from greater than 0 to less than 6, $6-nx$ is greater than or equal to 0, $n$ is the valence of A, and A is selected from the group consisting of halides, nitrate, sulfamate, sulfate and mixtures thereof;
   b. a zirconium compound selected from trioxodizirconium salts and the group having the general empirical formula:

$ZrO(OH)_{2-nz}B_z$ 

wherein Z may vary from 0.9 to 2, $n$ is the valence of B, $2-nz$ is greater than or equal to 0, and B is selected from the group consisting of halides, nitrate, sulfamate, sulfate and mixtures thereof;
   c. a hydroxy carboxylic compound selected from the group consisting of non-toxic salts of hydroxy carboxylic acids, non-toxic salts of aluminum chelates of hydroxy carboxylic acids, codried mixtures of aluminum hydroxide with non-toxic salts of aluminum chelates of hydroxy carboxylic acids, and mixtures thereof, said hydroxy carboxylic acids having a hydroxyl group alpha and/or beta to the carboxylic acid and being selected from the group consisting of lactic, citric, tartaric, glycolic, gluconic, trihydroxy glutaric, citryl trigluconic, citryl monogluconic, citryl digluconic, malic, tetrahydroxy adipic, and citramalic acids and mixtures thereof;
said zirconium and basic aluminum compounds being present in such amounts as to yield an Al/Zr mole ratio of about 10:1 to 1:10, and said hydroxy caboxylic compound being present in such an amount that the pH of a 5 to 15 weight percent (based on the oxides of Al and Zr) aqueous solution of the complex is at least about 3.

2. An astringent complex according to claim 1 wherein x varies from about 1 to about 2.

3. An astringent complex according to claim 1 wherein A is chloride.

4. An astringent complex according to claim 1 wherein the basic aluminum compound is a phenolsulfonate complex of the basic aluminum compound set forth in (a).

5. An astringent complex according to claim 1 wherein B is chloride and $z$ is about 1.

6. An astringent complex according to claim 1 wherein B is chloride and $z$ is about 2.

7. An astringent complex according to claim 1 wherein the cation of the non-toxic salts is selected from the group consisting of sodium, potassium, lithium, magnesium, calcium, zinc, zirconium, aluminum, ammonium and mixtures thereof.

8. An astringent complex according to claim 1 wherein the hydroxy carboxylic compound is selected from the group consisting of sodium lactate, potassium lactate, magnesium lactate and mixtures thereof.

9. An astringent complex according to claim 1 wherein said hydroxy carboxylic compound is selected from the group consisting of magnesium citryl mono-, di-, and trigluconates and mixtures thereof.

10. An astringent complex according to claim 1 wherein said hydroxy carboxylic compound is a sodium aluminum chlorhydroxy lactate.

11. An astringent complex according to claim 1 wherein said hydroxy carboxylic compound is sodium aluminum hydroxy lactate.

12. An astringent complex according to claim 1 wherein the Al/Zr mole ratio is about 1:1 to 4:1.

13. An astringent complex according to claim 1 wherein said complex also includes aluminum chloride.

14. An astringent complex according to claim 1 wherein said complex is in the form of a powder.

15. An anti-perspirant composition comprising an aqueous solution of the complex according to claim 1 wherein said complex is present in an amount such that the total amount of aluminum plus zirconium in the solution, calculated as the oxides, is about 5 to 15 weight percent.

16. A powder-in-oil anti-perspirant composition comprising an aerosol propellant and the complex according to claim 14 wherein said complex is present in an amount of about 1–6 weight percent of the anti-perspirant composition.

* * * * *